United States Patent [19]

Bailey

[11] 4,310,310

[45] Jan. 12, 1982

[54] LOCKING ASSEMBLY FOR DENTAL HANDPIECE

[75] Inventor: Ronald L. Bailey, St. Charles, Mo.

[73] Assignee: Young Dental Mfg. Co., Hazelwood, Mo.

[21] Appl. No.: 184,751

[22] Filed: Sep. 8, 1980

[51] Int. Cl.³ ............................................... A61C 1/08
[52] U.S. Cl. .................................................... 433/126
[58] Field of Search ......................................... 433/126

[56] References Cited

U.S. PATENT DOCUMENTS

| | | | |
|---|---|---|---|
| 2,010,421 | 8/1935 | Terry | 32/27 |
| 2,135,933 | 11/1938 | Blair | 433/126 |
| 2,370,632 | 3/1945 | Blair | 32/27 |
| 2,376,295 | 5/1945 | Wahlberg | 433/126 |
| 3,665,606 | 5/1972 | Saupe | 433/126 |
| 3,909,946 | 10/1975 | Watanabe | 32/27 |
| 3,955,284 | 5/1976 | Balson | 32/27 |
| 4,080,737 | 3/1978 | Fleer | 32/22 |
| 4,123,845 | 11/1978 | Fattaleh | 32/59 |
| 4,175,323 | 11/1979 | Eibofner et al. | 433/126 |

Primary Examiner—Robert Peshock
Attorney, Agent, or Firm—Rogers, Eilers & Howell

[57] ABSTRACT

A dental handpiece assembly has a handle sleeve with an exterior notch formed in its exterior surface. The head of the handpiece is mounted to a shoulder sleeve, which sleeve has a locking extension with an end lug size to be received within the handle notch. A locking ring is rotatably mounted on the handle, and has a slot sized to allow the locking extension to extend through it so that the lug is received within the handle notch. The exterior surface of the lock ring is approximately flush relative to the adjacent exterior surfaces of the handle and shoulder. A spring mounted to the handle and to the lock ring biases the lock ring to be positioned to block removal of the lug from the handle notch. The spring is mounted within the lock ring and on the outside of a third sleeve projecting unitarily from the first sleeve. A bearing sleeve acts as a bearing for a drive rod that extends through the bearing to transmit driving force to the tool in the head of the handpiece. The bearing acts to hold the lock ring against axial movement relative to the handle. The lug has a curved end surface so that when the shoulder sleeve is moved towards the handle for mounting thereto, the curved surface of the lug contacts the edge of the handle notch to guide the lug into the notch, and simultaneously rotates the lock ring to allow passage of the lug into the notch.

15 Claims, 7 Drawing Figures

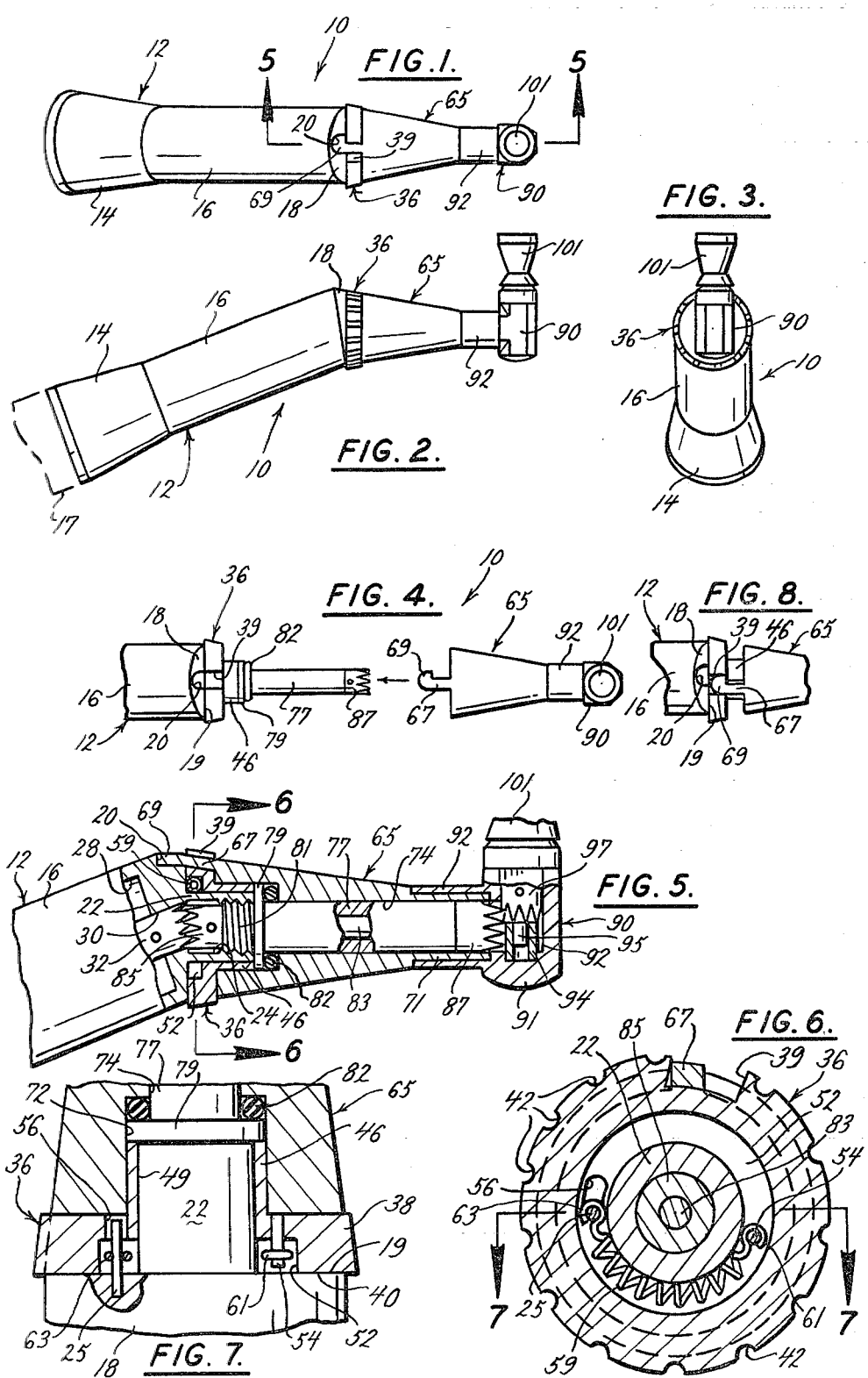

LOCKING ASSEMBLY FOR DENTAL HANDPIECE

BACKGROUND AND SUMMARY OF THE INVENTION

The present invention relates to dental handpiece assemblies having one sleeve which is to be detachably mounted in locked position to a second sleeve to allow driving force to be transmitted through the sleeves to drive a dental tool in the head of the handpiece. In the prior art there have been handpieces having means to hold one sleeve portion of a handpiece to another sleeve portion of a dental handpiece. However, those devices have not provided the ease in attachment and detachment and operational advantages provided by the present invention.

The present invention has a handle sleeve having a notch. A lock ring having a slot is rotatably mounted to a mounting sleeve projecting from the handle. A spring is mounted to the handle and to the locking ring, and biases the ring towards the notch so that it partially blocks the handle notch.

A shoulder sleeve has a locking extension with a lug on its end. The shoulder can be mounted to the locking ring so that the extension passes through the ring slot to allow the lug to come against the edge of the handle notch. The end surface of the lug is shaped so that when the lug is pushed towards the handle notch, the lug surface presses against the notch edge to guide the lug into the notch. As the lug is guided into the notch it also moves the lock ring to allow the lug to pass through the lock ring slot into the notch. After the lug enters the notch, the ring is rotated by the spring to block passage of the lug out of the notch, so that the lug can be locked without having to rotate the ring with the fingers.

In the preferred embodiment of the invention, the notch and slot are on the surfaces of the handle and ring respectively, so the operator can easily view the lug and ring to see if the lug is in the locked position. The operator can also lock the shoulder sleeve to the handle sleeve without looking at the two pieces, as by using his or her fingers to ascertain the location of the locking extension and the ring slot, the pieces can be moved to be locked. In the preferred embodiment, the spring is helical and is positioned against exposure by being hidden within the ring. The spiral spring provides biasing action, while allowing deformation of spring length to be only a small fraction of the overall spring length. In the preferred embodiment, the spiral spring is mounted at one end to a pin extending from the handle and at the other end to a pin extending from the lock ring, and the ring has an aperture which receives the handle pin to prevent overextension of the spring. The preferred embodiment features the surface of the ring being approximately flush with the surfaces of its adjacent shoulder and handle sleeves so that it does not protrude, to thus prevent accidental operation. A bearing for a rod connecting drive gears is used to hold the lock ring to the handle.

DESCRIPTION OF THE DRAWINGS

FIG. 1 is a plan view of the dental handpiece showing the shoulder section locked to the handle section, with the flutes of the lock ring, not shown, for clarity;

FIG. 2 is a side elevation of the handpiece;

FIG. 3 is an end plan view of the handpiece taken on the line 3—3 of FIG. 2;

FIG. 4 is an exploded view of the handpiece showing the shoulder section detached from the handle with the ring flutes not shown, and with the ring shown rotated to the "unlock" position;

FIG. 5 is a section of the handpiece taken on the line 5—5 of FIG. 1, showing the bearing sleeve broken;

FIG. 6 is a section taken on the line 6—6 of FIG. 5;

FIG. 7 is a section taken on the line 7—7 of FIG. 6; and

FIG. 8 is a partial plan view showing the locking lug within the ring slot ready for movement into the handle notch.

DESCRIPTION OF THE PREFERRED EMBODIMENT

The drawings show a handpiece 10 having a handle sleeve 12, the handle 12 having an enlarged tapered section 14 at its outer end which extends into a cylindrical section 16. The tapered section 14 can be secured to another section 17, a portion of which is shown in dashed lines in FIG. 2. At its inner end handle 12 bends from section 16 into a short slanted end section 18 which has a flat end surface 19. The exterior surface of section 18 has a U-shaped notch 20, as seen clearly in FIG. 4, for receiving the lug of a hook to be described. Projecting from the handle end surface 19 is a unitary cylindrical sleeve 22 having an internally threaded cylindrical bore 24. A pin 25 fits tightly as by a press fit, within a cylindrical bore into the end surface 19.

Handle 12 has an enlarged cylindrical bore 28 which extends from the outer end of section 14 to the inner end of the handle where it intersects with a smaller cylindrical bore 30, with bore 30 intersecting bore 24, as seen in FIG. 5. A drive shaft (not shown) extends through handle 12 and is mounted to a bevel gear 32 by a pin.

Mounted for rotation relative to handle 12 is a lock ring 36, shown enlarged in FIGS. 6 and 7. Ring 36 has an annular section 38 whose flat outer end 40 fits flush against the flat end surface 19 of handle section 18, so that the two surfaces can slide smoothly relative to each other when the ring 36 is rotated relative to the handle.

The outer surface of annular section 38 has a slot 39 which can be aligned with U-notch 20, as shown in FIG. 4, when ring 36 is in the unlocked position, as will be described.

The ring annular section 38 has a plurality of longitudinal gripping flutes 42 in its outer surface, which are not shown in FIGS. 1 and 8 for purposes of clarifying the location of slot 39. Extending inwardly from the rim of ring annular section 38 is a unitary cylindrical sleeve 46 which has a cylindrical bore 49. Bore 49 telescopically slidingly receives the exterior surface of handle sleeve 22 with the flat inner end of sleeve 46 being flush with the flat end of sleeve 22. The ring annular section 38 has a cylindrical recess 52 of larger diameter than the sleeve 22 diameter, so that an annular cavity is formed between ring 36 and sleeve 22.

Ring section 38 has a small cylindrical bore which tightly receives, as by a press fit, a pin 54. On the side of lock ring 36 opposite pin 54, is formed a small aperture 56, which receives the inner end of pin 25, as seen in FIGS. 6 and 7, so that pin 25 serves as a stop for rotation of lock ring 36.

A helical spring 59 has hooked ends 61 and 63 which fit about pins 54 and 25, respectfully, so that the spring 59 is mounted to curve within ring recess 52 between sleeve 22 and annular section 38. Spring 59 acts to bias ring 36 in the clockwise direction (as viewed looking at FIG. 6) relative to handle 12, so that ring 36 has a position shown in FIGS. 1, 6 and 7 that partially blocks handle notch 20. The stop pin 25 rests against the lower end (FIG. 6) of ring aperture 56 to prevent further clockwise rotation in the FIG. 6 position.

To the inside of handle 12 is a tapered shoulder sleeve 65. The outer end of shoulder 65 has a tongue 67 which has a locking lug 69 formed at its outer end that is sized to be received within the handle notch 20. The tongue 67 and lug 69 together form a generally J-shaped hook. As seen in FIGS. 1 and 4, the tongue 67 is of less width than the width of ring notch 39, so that the spring 59 can bias the ring 36 to cause part of the ring to block handle notch 20, thus capturing the lug 69 within notch 20 to lock the shoulder 65 to the handle 12. The ring 36 can be rotated to align slot 39 with handle notch 20, which allows lug 69, which is of slightly less width than ring slot 39, to pass through slot 39 to allow disengagement of shoulder 65 from handle 12.

Shoulder 65 is of a generally conical shape, and at its inner end extends into a cylindrical neck sleeve 71. Shoulder 65 has, at its outer end, a cylindrical bore 72 which slidingly receives telescopically the sleeve 46 of lock ring 36. Bore 72 extends inwardly into a smaller cylindrical bore 74, which slidingly receives a cylindrical bearing sleeve 77. At its outer end sleeve 77 has a cylindrical flange 79 which is slidingly received within bore 72. Bearing 77 has, extending outwardly from flange 79, a threaded portion 81 which screws into the threads of handle sleeve 22 so that the flat outer end of flange 79 mounts flush against the flat inner surfaces of handle sleeve 22 and ring sleeve 46, as seen in FIGS. 5 and 7, to hold the lock ring in the position shown in FIGS. 6 and 7.

An annular rubber washer 82 is mounted about bearing sleeve 77 adjacent the inner end of circular flange 79 so as to fit within bore 72.

The ring 36 fits with handle 12 and shoulder 65 so that the exterior surface of ring 36 is approximately flush with the adjacent exterior surfaces of handle 12 and shoulder 65 to eliminate snagging protrusions.

Bearing sleeve 77 has a cylindrical bore extending through it which telescopically and rotatably receives a shaft 83 (shown partially in FIG. 5), which is mounted at its ends by pins to bevel gear 85 and bevel gear 87. Gear 85 rotates within bore 24 of sleeve 22, and drives gear 87 which is sized to be telescopically received within shoulder sleeve bore 74.

A cross head 90 has a cylindrical collar 92 with a cylindrical bore which telescopically snugly receives the cylindrical neck 71, so that the collar 92 can be mounted and dismounted about collar 71 by the hands. The head 90 has a closed end 91 with a cylindrical bore 92 extending therefrom towards the other open end of the head. A bearing sleeve 94 is mounted within a conforming cylindrical bore at the closed end of the head. The bearing sleeve 94 has an inner bore which receives a shaft 95 of a driven gear 97 which is meshed with gear 87 to be driven thereby. Gear 97 has a typical connection to a dental tool, such as a cleaning cup 101, so that rotation of gear 97 rotates cup 101.

The handle sleeve 12, shoulder sleeve 65, head 90, and lock ring 36 can all be of aluminum. The exterior surface of ring 36 can be anodized to have a surface color desired for purposes of better visibility of the ring surface, and to code for different sized shoulder sleeves with which it is to be used. The flutes 42 can be cut in ring 36 after it is anodized.

The bearing sleeve 77, the gears, the spring, and bearing 94 can all be of stainless steel.

OPERATION

The description of the operation will begin with the shoulder sleeve 65 mounted and locked to the handle 12, as shown in FIGS. 1-3 and 5-7. In this position the handpiece can be operated for use with a patient by gripping the handle 12 and moving the head 90 and dental cup 101 into position for operation. The rotation of gear 32 rotates gears 85 and 87, and in turn rotates gear 97 and cup 101. The tongue 67 and lug 69 being locked to the ring and handle not only permits the shoulder 65 from being pulled loose from the ring and handle, but prevents rotation of the shoulder relative to the handle. With the ring 36 approximately flush with the shoulder and handle, snagging by protrusions and accidental disengagement is minimized. When the head and shoulder are pressed towards the handle, the compressive force is distributed over the entire area of the ring, rather than over a small area.

After performing the particular service upon the patient, the shoulder sleeve 65 can be easily removed from the handle. The operator can grasp the handle with his left hand so that his left index finger rests on the surface of ring 36 and the other three fingers curve about handle sections 16 and 14. The left hand thumb is placed against the surface of lock ring 36 directly opposite the index finger. The right hand fingers and thumb grasp about the shoulder sleeve 65 and the head 90. The left hand index finger and thumb then rotate the lock ring 36 counterclockwise (viewed looking at FIG. 6), against the bias of spring 59, until the stop pin 25 rests against the upper end of the ring aperture 56 to block further rotation of the ring relative to the handle 12 and the shoulder 65. In this position, the ring slot 39 is aligned with the handle notch 20, as shown in FIG. 4.

The right hand can then pull the head 90 and shoulder 65 away from ring 36 and handle 12 so that lug 69 is pulled out of handle notch 20 and through ring slot 39, to completely disengage shoulder 65 from the ring and handle, as shown in FIG. 4.

After disengagement, the ring 36 can be released to allow it and the spring 59 to return to the FIG. 6 position.

To mount the shoulder 65 to the handle, the left hand rotates the ring 36 to align ring slot 39 with handle notch 20. The right hand moves shoulder 65 so that its bore 74 receives the gear 87 and the bearing 77. The shoulder 65 is thence continued to be moved towards the lock ring until lug 69 fits within ring slot 39, as shown in FIG. 8. In this position the outer curved surface of lug 69 rests against the inner surface 19 of handle section 18. In this position, about one-half of the lug 69 is in alignment with the handle notch 20, as shown in FIG. 8, with the curved outer end of lug 69 resting upon the corner 103 of the notch 20. From this FIG. 8 position, as the shoulder 65 is pressed towards the handle 12, the notch corner 103 presses against the curved surface of the lug 69 to guide the lug towards reception within the notch 20. As the lug 69 moves into notch 20, it presses against the upper wall of ring slot 39 to rotate the ring 36 in the counterclockwise direction (viewed looking at FIG. 6) so that as the tongue 67 and lug 69 move towards the handle, the lock ring notch 39 moves towards alignment with the notch 20 to allow lug 69 to move into notch 20, as shown in FIG. 1.

After the lug 69 is pushed past the outer edge of lock ring 36, the bias of spring 59 rotates the ring to position the ring slot 39 so that the ring partially blocks the notch 20, to prevent the lug from being pulled out of the notch 20, as shown in FIG. 1.

The shoulder 65 can thus be engaged and locked to the handle 12 without using a hand to rotate the ring 36. The engaging and locking can be done in one smooth and quick motion. The shoulder 65 and head 90 can be locked and engaged even while the gear is rotating.

Because the slot 39 is on the surface of the ring, and the notch 20 is on the surface of the handle, the operator can easily view the lug 69 and ring 36 to see if the lug is locked into position. With the present arrangement, the operator can lock the shoulder without even looking at the pieces, by using his or her fingers to determine the location of the tongue and lug, and of the ring slot, and then moving the parts together as described.

The lock ring is held on securely, and the spring is positioned against exposure by being hidden within the ring. The spiral spring provides biasing action while allowing deformation of spring length which is a small fraction of the overall spring length. The step pin 25 and ring aperture prevent overextension of the spring.

There are various changes and modifications which may be made to applicant's invention as would be apparent to those skilled in the art. However, any of these changes or modifications are included in the teaching of applicant's disclosure and he intends that his invention be limited only by the scope of the claims appended hereto.

I claim:

1. A connection assembly for a dental handpiece comprising:
    (a) a first sleeve having a first end and a second end, and having an exterior surface with an exterior notch formed in said exterior surface, the notch extending longitudinally relative to the first sleeve, the notch having an edge that opens the notch towards the first end of the first sleeve;
    (b) a second sleeve having a first end and a second end with a locking extension projecting longitudinally from the second end of the second sleeve, the extension having a lug sized to be received within the said notch; and
    (c) a locking ring with means for being rotatably mounted to the first sleeve to rotate from a first locking position to a second unlocking position, the ring having an exterior surface with a longitudinal slot formed therein sized to allow passage of the lug and extension therethrough so that in the second ring position the ring slot is aligned with the first sleeve notch to allow the lug to be longitudinally moved through the ring slot into the first sleeve notch, and in the second ring position part of the ring surrounding the slot blocks removal of the lug from the notch.

2. The structure of claim 1 further comprising means for rotatably biasing the ring relative to the first sleeve towards the second position blocking removal of the lug from the notch.

3. The structure of claim 2 wherein the lug has a surface with means for pressing against the edge of the notch so that as the lug moves through the slot towards the notch, the engagement of the said lug surface with the first end of the first sleeve at the intersection with the notch edge, rotates the ring slot into alignment with the notch and guides the lug into the notch.

4. The structure of claim 3 wherein the lug surface with means for pressing is a curved surface.

5. The structure of claim 1 wherein the ring has an inner recess, and wherein the means for biasing the ring is located within the said recess and is connected to the first sleeve and to the ring.

6. The structure of claim 5 wherein the locking extension with its lug is of a generally "J" shape.

7. The structure of claim 5 further comprising a third sleeve mounted to and projecting from the first sleeve, with the ring fitting around the third sleeve, and with the biasing means located between the third sleeve and the ring.

8. The structure of claim 7 further comprising a holding member engaged to the third sleeve and to the ring to hold the ring from axial movement relative to the third sleeve.

9. The structure of claim 8 wherein the holding member is a bearing sleeve having a flange that engages the ring.

10. The structure of claim 9 wherein the ring has a unitary sleeve that extends towards the second sleeve, with an end approximately flush with an end of the third sleeve.

11. The structure of claim 1 wherein the exterior surface of the locking ring is approximately flush relative to the adjacent exterior surfaces of the first and second sleeves.

12. A connection assembly for a dental handpiece comprising:
    (a) a first sleeve having a first end and a second end, and having an exterior surface with an exterior notch formed in said exterior surface, the notch extending longitudinally relative to the first sleeve, the notch having an edge that opens the notch towards the first end of the first sleeve;
    (b) a second sleeve having a first end and a second end with a rigid locking extension projecting longitudinally from the second end of the second sleeve, the extension having a tongue section and a lug of larger width than the tongue, the lug being sized to be received within the said notch;
    (c) a locking ring with means for being rotatably mounted to the first sleeve to rotate from a first locking position to a second unlocking position, the ring having an exterior surface with a longitudinal slot formed therein sized to allow passage of the lug and extension therethrough so that in the second ring position the ring slot is aligned with the first sleeve notch to allow the lug to be longitudinally moved through the ring slot into the first sleeve notch, and in the second ring position part of the ring surrounding the slot blocks removal of the lug from the notch;
    (d) means for rotatably biasing the ring relative to the first sleeve towards the second position blocking removal of the lug from the notch; and
    (e) the lug having a surface for pressing against the edge of the notch so that as the lug moves through the slot towards the notch, the engagement of the said lug surface with the first end of the first sleeve at the intersection with the notch edge, rotates the ring slot into alignment with the notch and guides the lug into the notch.

13. The structure of claim 12 wherein the ring has an inner recess, and wherein the means for biasing the ring is located within the said recess and is connected to the first sleeve and to the ring.

14. The structure of claim 13 further comprising a third sleeve mounted to and projecting from the first sleeve, with the ring fitting around the third sleeve, and with the biasing means located between the third sleeve and the ring, and a bearing sleeve engaged to the third sleeve and to the ring to hold the ring from axial movement relative to the third sleeve.

15. A connection assembly for a dental handpiece comprising:
   (a) a first sleeve having a first end and a second end, and having an exterior surface with an exterior notch formed in said exterior surface, the notch extending longitudinally relative to the first sleeve, the notch having an edge that opens the notch towards the first end of the first sleeve;
   (b) a second sleeve having a first end and a second end with a rigid locking extension projecting longitudinally from the second end of the second sleeve, the extension having a tongue section and a lug of larger width than the tongue, the lug being sized to be received within the said notch; and
   (c) a locking ring with means for being rotatably mounted to the first sleeve to rotate from a first locking position to a second unlocking position, the ring having an inner recess, and having an exterior surface with a longitudinal slot formed therein sized to allow passage of the lug and extension therethrough so that in the second ring position the ring slot is aligned with the first sleeve notch to allow the lug to be longitudinally moved through the ring slot into the first sleeve notch, and in the second ring position part of the ring surrounding the slot blocks removal of the lug from the notch, the ring having a unitary sleeve that extends towards the second sleeve, with an end of said ring unitary sleeve approximately flush with an end of the third sleeve;
   (d) means for rotatably biasing the ring relative to the first sleeve towards the second position blocking removal of the lug from the notch, said biasing means being located within the said ring recess and being connected to the first sleeve and to the ring;
   (e) the lug having a curved surface for pressing against the edge of the notch so that as the lug moves through the slot towards the notch, the engagement of the said lug surface with the first end of the first sleeve at the intersection with the notch edge, rotates the ring slot into alignment with the notch and guides the lug into the notch;
   (f) a third sleeve mounted to and projecting from the first sleeve, with the ring fitting around the third sleeve, and with the biasing means located between the third sleeve and the ring; and
   (g) a bearing sleeve having a flange, the bearing sleeve being engaged to the third sleeve so that the flange fits against the ring sleeve to hold the ring from axial movement relative to the third sleeve.

* * * * *